United States Patent [19]  [11] 3,939,191
Asano et al. [45] Feb. 17, 1976

[54] PROCESS FOR METHANOL SYNTHESIS

[75] Inventors: Setunobu Asano; Tadasi Nakamura, both of Niigata, Japan

[73] Assignee: Mitsubishi Gas Chemical Co. Inc., Tokyo, Japan

[22] Filed: Dec. 18, 1973

[21] Appl. No.: 425,830

[30] Foreign Application Priority Data
July 24, 1972 Japan.................. 47-73468

[52] U.S. Cl............................. 260/449.5; 252/432
[51] Int. Cl.²....................................... C07C 29/16
[58] Field of Search................ 260/449.5, 449 R

[56] References Cited
UNITED STATES PATENTS

| | | |
|---|---|---|
| 1,818,165 | 8/1931 | Schmidt et al.................. 260/449.5 |
| 1,920,373 | 8/1933 | Gosselin........................... 260/449 |
| 1,977,718 | 10/1934 | Dreyfus............................ 260/449 |
| 3,256,208 | 6/1966 | Eguchi et al..................... 260/449.5 |

*Primary Examiner*—Bernard Helfin
*Assistant Examiner*—A. Siegel
*Attorney, Agent, or Firm*—Armstrong, Nikaido & Wegner

[57] ABSTRACT

Catalyst comprising oxides of copper, zinc and boron in an atomic ratio of copper: zinc: boron of 20 to 70: 15 to 50: 0.3 to 5.3 is used for methanol synthesis from hydrogen and carbon oxides at a reaction pressure of 20 to 500 kg/cm², reaction temperature of 150° to 350°C and space velocity of 2,000 to $5 \times 10^4$ hr$^{-1}$.

The catalyst has a higher catalytic efficiency, and improved heat resistance and durability.

2 Claims, No Drawings

PROCESS FOR METHANOL SYNTHESIS

This invention relates to a novel catalyst for synthesizing methanol, and more particularly to a novel catalyst having a high catalytic activity and good heat resistance and durability, suitable for the methanol synthesis at a relatively low pressure.

Heretofore, catalysts consisting of copper and zinc, or copper, zinc and chromium have been widely used as the catalysts for synthesizing methanol from carbon monoxide and hydrogen. However, the three-component catalysts consisting of copper, zinc and chromium have a better durability and heat resistance than the two-component catalysts consisting of copper and zinc, but these three-component and two-component catalysts are generally poor in the heat resistance and durability, and cannot serve in a prolonged use. Furthermore, these catalysts have a high activity initially, but their catalytic activities are considerably reduced during the service, and it is very difficult to maintain the initial high activity continuously. That is, the low catalytic activity is generally their disadvantage.

A low pressure methanol synthesis is disclosed in Japanese Patent Publication No. 16682/70 that three-component catalysts consisting of copper, zinc and aluminum are suitable for the low pressure methanol synthesis.

The present inventors have made studies on the two-component catalysts consisting of copper and zinc, and, as a result, have found that the addition of boron as the third component to the two-component system of copper and zinc can increase the catalytic activity considerably and improve the heat resistance and durability very highly at the same time, and have established the present invention.

That is to say, the present invention provides a novel three-component catalyst comprising oxides of copper, zinc and boron for methanol synthesis.

The boron, one of the components constituting the catalyst of the present invention, has been so far utilized as a component of the catalyst for oxidation reaction, but there has been no example of using the boron as a component of the catalyst for hydrogenation reaction. When the boron is used as a component of the methanol synthesis catalyst, the catalyst has a better catalytic activity than those of the conventional catalysts of copper-zinc system or copper-zinc-chromium system, and also has a higher heat resistance and durability.

The catalyst of the present invention comprises oxides of copper, zinc and boron in an atomic ratio of copper: zinc: boron of 20 to 70: 15 to 50: 0.3 to 5.3. It is particularly preferable that the boron is contained in the atomic ratio of 0.5 to 3.5. If the boron content exceeds said upper limit, the catalytic activity will be considerably lowered.

As the copper and zinc sources for the present catalyst, the same water-soluble salts as used in the preparation of the conventional catalysts of the copper-zinc catalyst, for example, copper nitrate, zinc nitrate, etc. can be used.

As the boron source, water-soluble boron compounds such as borax, ammonium borate, boric acid, etc. can be used.

The present catalyst can be prepared according to the kneading method, coprecipitation method, etc, but it is particularly preferable to prepare the present catalyst according to the coprecipitation method. That is, water soluble salts of metal components constituting the present catalyst are dissolved in water, and mixed. Then, carbonates, bicarbonates or hydroxides of alkali metal are added to the mixture and mixed together. The resulting precipitates are filtered and washed, and then calcined, molded into tablets, crushed, and reduced according to the conventional method, whereby the present catalyst is prepared. The coprecipitation is carried out at a temperature from room temperature to 130°C, but heating to 50°– 95°C is preferable to the room temperature.

The thus prepared catalyst of the present invention has a considerably improved heat resistance and durability and a higher catalytic activity, as compared with the conventional catalysts of copper-zinc system, and are very suitable for the methanol synthesis. The methanol synthesis can be carried out with the present catalyst at a lower pressure than with the conventional catalysts, and has a sufficient catalytic activity even at such a lower temperature and can suppress production of by-products.

Feed gas having the composition as so far used can be also fed, as such, to the present catalyst, and there is no special restriction to the composition of the feed gas. Methanol can be synthesized from hydrogen and carbon oxides in the presence of the present catalyst at a reaction pressure of 20 to 500 kg/cm$^2$, preferably 30 to 150 kg/cm$^2$, a reaction temperature of 150° to 350°C. preferably 200° to 280°C, and a space velocity of 2000 to $5 \times 10^4$ hr$^{-1}$.

The present catalyst has a good activity as methanol synthesis catalyst, but can be also used as catalysts for carbon monoxide conversion, hydrogenation, and methanol decomposition. These reactions can be effectively carried out by properly selecting their specific reaction conditions.

Now, the present invention will be explained in detail by way of examples.

EXAMPLE 1

80 g (0.331 mole) of cupric nitrate trihydrate, and 74 g (0.249 moles) of zinc nitrate hexahydrate were dissolved in 2000 ml of deionized water to prepare a solution No. 1. 23.6 g (0.0619 moles) of borax was dissolved in 150 ml of deionized water, neutralized with nitric acid, and adjusted to pH 6 to prepare a solution No. 2. 67.6 g (0.638 moles) of sodium carbonate was dissolved in 2000 ml of deionized water to prepare a solution No. 3.

Said solutions Nos. 1 and 2 were mixed together, and then the resulting mixture was mixed with the solution No. 3 while sufficiently stirring the mixture. The mixture was continuously stirred for 3 hours, and the resulting precipitates were filtered and washed. Then, the precipitates were dried overnight at 80°C, calcined at 380°C for 2 hours while passing air over the precipitates, and then molded into tablets, using graphite. The resulting catalyst tablets had an atomic ratio of Cu: Zn: B = 59.9 : 38.7 : 1.4. The tablets were then crushed to sizes of 20 to 42 meshes (Tyler) and reduced with a methanol synthesis gas at an atmospheric pressure. The reduction temperature were slowly elevated to suppress an abrupt heat release due to the reduction reaction, and the reduction was carried out finally at 240°C for 2 hours to prepare a catalyst A.

The thus obtained catalyst A was subjected to a methanol synthesis test under the following conditions.

That is, a feed gas having the following inlet gas composition of 67 % of hydrogen, 25 % of carbon monoxide, 5 % of carbon dioxide, 1 % of methane and 2 % of nitrogen (by volume) was passed over the catalyst at a reaction pressure of 150 kg/cm$^2$, reaction temperature of 240°C and space velocity of 10,000 hr$^{-1}$, and its catalytic activity was represented by the methanol concentration in outlet gas. The result is shown in Table 1. For comparison, the results of activities of catalysts of copper-zinc system (Catalyst B), copper-zinc-chromium system (Catalyst C), and copper-zinc-aluminum system (Catalyst D) prepared in the following manners, respectively, are shown together in Table 1.

a. Preparation of Comparative Catalyst B:

32.6 g (0.135 moles) of cupric nitrate trihydrate, and 40.1 g (0.135 moles) of zinc nitrate hexahydrate, were dissolved in 1600 ml of deionized water to prepare a solution No. 1. 31.5 g of sodium carbonate was dissolved in 800 ml of deionized water to prepare a solution No. 2.

The resulting solutions Nos. 1 and 2 were mixed with stirring, and then the mixture was further stirred for 3 hours. The resulting precipitates were filtered and washed, and then subjected to the same operations as used in the case of the Catalyst A preparation, to prepare Catalyst B.

b. Preparation of Comparative Catalyst C:

23.3 g (0.0964 moles) of cupric nitrate trihydrate, 23.3 g (0.0783 moles) of zinc nitrate hexahydrate, and 23.3 g (0.0582 moles) of chromic nitrate were dissolved in 900 ml of water to prepare a solution No. 1. 36.5 g (0.3447 moles) of sodium carbonate was dissolved in 1,200 ml of water to prepare a solution No. 2. Then, the solution No. 2 was added to the solution No. 1, while sufficiently stirring the solution No. 1. After the completion of addition, the mixture was stirred for 2 hours, and the resulting precipitates were filtered and washed, and then subjected to the same operations as used in the case of the catalyst A preparation, to prepare Catalyst C.

c. Preparation of Comparative Catalyst D:

5.7 g (0.069 moles) of sodium aluminate was dissolved in 100 ml of water, and then admixed with 18 ml (0.2415 moles) of concentrated nitric acid (specific gravity: 1.38). The resulting solution was further mixed with a solution containing 100 g (0.414 moles) of cupric nitrate trihydrate and 61.6 g (0.207 moles) of zinc nitrate hexahydrate dissolved in 2,500 ml of water to prepare a solution No. 1. 109.4 g (1.032 moles) of sodium carbonate was dissolved in 4,200 ml of water to prepare a solution No. 2.

The solutions Nos. 1 and 2 were heated separately to 75°– 80°C, and mixed together while sufficiently stirring these solutions. After the mixing, the resulting mixture was stirred for about 2 hours, and then filtered and washed, and subjected to the same operations as used in the case of the Catalyst A preparation, to prepare Catalyst D.

To determine the durability of the catalyst, the results of activity test after the synthesis at 360°C are shown together in Table 1.

Table 1

| | Methanol concentration in outlet gas (% by mole) | | |
|---|---|---|---|
| | Initial activity | After 2 hours at 360°C | After 20 hours at 360°C |
| Catalyst A | 42.0 | 38.0 | 32.0 |
| Catalyst B | 30.0 | 15.0 | 5.0 |
| Catalyst C | 21.0 | 24.0 | 14.0 |
| Catalyst D | 35.0 | 32.0 | 25.0 |

EXAMPLE 2

80 g (0.331 mole) of cupric nitrate trihydrate and 49.2 g (0.165 moles) of zinc nitrate hexahydrate were dissolved in about 800 ml of water to prepare a solution No. 1. 31.1 g (0.0829 moles) of borax was dissolved in 300 ml of water to prepare a solution No. 2. 60.6 g (0.573 moles) of sodium carbonate was dissolved in 1,300 ml of water to prepare a solution No. 3.

First of all, nitric acid was added to the solution No. 2 to adjust pH to about 5, and then mixed with the solution No. 1 to prepare a solution No. 4. The solution No. 4 was added to the solution No. 3, while sufficiently stirring the solution No. 3, and the resulting mixture was further stirred for about 3 hours. The resulting precipitates were filtered and washed, and then subjected to drying, calcination, molding into tablets, crushing and reduction in the same manner as in the case of the Catalyst A preparation of Example 1.

The resulting catalyst had an atomic ratio of Cu : Zn: B = 65.9 : 31.8 : 2.3. (which will be hereinafter referred to as Catalyst E) was subjected to activity test for methanol synthesis, using a feed gas having the same composition as used in Example 1, at a reaction pressure of 140 kg/cm$^2$, reaction temperature of 280°C and space velocity of 5 × 10$^4$ hr$^{-1}$. The methanol concentration in outlet gas at that time is shown in Table 2.

Table 2

| | Methanol concentration in outlet gas (% by mole) | | |
|---|---|---|---|
| | Initial activity | After 2 hours at 360°C | After 20 hours at 360°C |
| Catalyst E | 23.0 | 19.0 | 17.0 |

EXAMPLE 3

30 g (0.1242 moles) of cupric nitrate trihydrate, 27.7 g (0.0932 moles) of zinc nitrate hexahydrate and 5.8 g (0.0938 moles) of boric acid were dissolved in about 1,000 ml of deionized water to prepare a solution No. 1. 27.7 g (0.213 moles) of sodium carbonate was dissolved in about 1,000 ml of deionized water to prepare a solution No. 2. The solutions Nos. 1 and 2 were mixed together, and then subjected to the same operations as used in the case of the Catalyst A preparation of Example 1, to prepare Catalyst F. The Catalyst thus prepared had an atomic ratio of Cu : Zn : B = 57.0 : 42.0 : 1.0. The catalyst was subjected to activity test at a space velocity of about 13,000 hr$^{-1}$, pressure of 60 kg/cm$^2$ or 100 kg/cm$^2$ and the temperature given in Table 3, using a feed gas having the following inlet gas composition: 4.83 % of carbon monoxide, 2.45 % of carbon dioxide, 68.07 % of hydrogen, 0.32 % of methane and 24.33 % of nitrogen (by volume). The result is shown in Table 3.

Table 3

| Reaction pressure | Methanol concentration in outlet gas (% by mole) Reaction temperature | | |
|---|---|---|---|
| | 220°C | 235°C | 250°C |
| 100 kg/cm² | 3.5 | 4.5 | 6.0 |
| 60 kg/cm² | 1.0 | 2.0 | 4.0 |

EXAMPLE 4

Catalyst having an atomic ratio of Cu : Zn : B = 57.6 : 41.9 : 0.5 (Catalyst G) and catalyst having an atomic ratio of Cu : Zn : B = 75.3 : 23.9 : 0.8 (Catalyst H) were prepared in the manner similar to that of Example 1, using the reagents similar to those of Example 1, and subjected to activity test under the same reaction conditions as in Example 1, using the same feed gas as used in Example 1. The results are given in Table 4

Table 4

| | Methanol concentration in outlet gas (% by mole) | | |
|---|---|---|---|
| | Initial activity | After 2 hours at 360°C | After 20 hours at 360°C |
| Catalyst G | 38.0 | 30.0 | 25.0 |
| Catalyst H | 40.0 | 31.0 | 27.0 |

As is apparent from the foregoing examples, the present catalyst has a very high catalytic activity, and is useful for low pressure methanol synthesis.

What is claimed is:

1. In a process for synthesizing methanol by the reaction of hydrogen and an oxide of carbon, the improvement which comprises carrying out the reaction in the presence of a catalyst comprising oxides of copper, zinc and boron in an atomic ratio of copper: zinc: boron of 20 to 70: 15 to 50: 0.3 to 5.3 at a reaction pressure of 20 to 500 kg/cm², a reaction temperature of 150° to 350°C and a space velocity of 2,000 to $5 \times 10^4$ hr$^{-1}$.

2. A process according to claim 1, wherein the reaction pressure is 30 to 150 kg/cm² and the reaction temperature is 200° to 280°C.

* * * * *